(12) United States Patent
Bellini et al.

(10) Patent No.: US 6,632,802 B2
(45) Date of Patent: Oct. 14, 2003

(54) HYALURONIC ACID ESTERS, THREADS AND BIOMATERIALS CONTAINING THEM, AND THEIR USE IN SURGERY

(75) Inventors: Davide Bellini, Montegrotto Terme (IT); Lanfranco Callegaro, Thiene (IT)

(73) Assignee: Fidia Advanced Biopolymers S.r.l., Abano Terme (IT)

( * ) Notice: Subject to any disclaimer, the term of this patent is extended or adjusted under 35 U.S.C. 154(b) by 15 days.

(21) Appl. No.: 09/941,055

(22) Filed: Aug. 28, 2001

(65) Prior Publication Data

US 2002/0026039 A1 Feb. 28, 2002

Related U.S. Application Data

(63) Continuation-in-part of application No. 09/236,958, filed on Jan. 25, 1999, now abandoned, which is a continuation-in-part of application No. PCT/EP97/04684, filed on Aug. 28, 1997.

(30) Foreign Application Priority Data

Aug. 29, 1996 (IT) .......................................... PD96A0207

(51) Int. Cl.[7] .......................... A61K 31/715; C08B 37/00
(52) U.S. Cl. ........................................... 514/54; 536/53
(58) Field of Search ................................ 514/54; 536/53

(56) References Cited

FOREIGN PATENT DOCUMENTS

| EP | 0216453 | * | 6/1986 |
| EP | 0216453 | * | 4/1987 |
| EP | 0341745 | * | 11/1989 |
| WO | 9524429 | * | 9/1995 |
| WO | 9707833 | * | 3/1997 |
| WO | 9808876 | * | 3/1998 |

OTHER PUBLICATIONS

Patent Abstracts of Japan 06025306, Feb. 1, 1994.*
Surgery, Gynecology & Obstetrics, vol. 161, pp. 213–222 (Sep. 1985), "A New Synthetic Monofilament Absorbable Suture Made from Polytrimethylene Carbonate", Abraham R. Katz, M.S. et al.*
J. Biomedical Mat. Res., vol. 13, pp. 477–496 (1979), "A Comparative Study of Poly(Glycolic Acid) and Catgut as Suture Materials. Histomorphology and Mechanical Properties", Andrea Pavan et al.*
Biomaterials 16, pp. 1283–1289 (1995), "Quantitative Analysis of the Inflammatory Reaction Surrounding Sutures Commonly Used in Operative Procedures and the Relation to Postsurgical Adhesion Formation", E.A. Bakkum et al.*
Surgery, Gynecology & Obstetrics, vol. 131, pp. 701–716 (Oct. 1970), "Evaluation of Tensile and Absorption Properties of Polyglycolic Acid Sture", Abraham R. Katz, M.S. et al.*

* cited by examiner

Primary Examiner—Kathleen K. Fonda
(74) Attorney, Agent, or Firm—Hedman & Costigan, P.C.

(57) ABSTRACT

The application discloses esters of hyaluronic acid, wherein a first part of the carboxylic functions is esterified with an araliphatic alcohol and a second part is esterified with at least one long-chain, straight aliphatic alcohol with between 10 and 22 carbon atoms. The possible remaining non-esterified carboxylic functions, if present, are salified. The application further discloses biocompatible threads having a multifilament conformation comprising filaments formed by the aforesaid esters, and their use in the fields of medicine and surgery.

18 Claims, 7 Drawing Sheets

HYALURONIC ACID ESTERS, THREADS AND BIOMATERIALS CONTAINING THEM, AND THEIR USE IN SURGERY

This application is a continuation-in-part of Ser. No. 09/236,958, filed Jan. 25, 1999, now abandoned which was a continuation-in-part of PCT Application PCT/EP97/04684, filed Aug. 28, 1997, which claimed the benefit of Italian Application Serial No. PD96A000207, filed Aug. 29, 1996.

FIELD OF THE INVENTION

The present invention concerns the preparation of a new series of ester derivatives of hyaluronic acid, biocompatible threads in a multifilament conformation comprising filaments constituted by such derivatives, and their use in the fields of medicine and surgery.

BACKGROUND ART

Suture threads are now widely used in modern surgical practice and can be made of a wide range of materials, according to the type of surgery to be performed (Abraham R. Katz et al. "A new synthetic monofilament absorbable suture made from polytrimethylene carbonate" Surgery, Gynecology & Obstetrics, September 1985, vol. 161, pages 213–222; Abraham R. Katz et al. "Evaluation of tensile and absorption properties of polyglycolic acid sutures" Surgery, Gynaecology & Obstetrics, October 1970, vol. 131, pages 701–716). It is possible, therefore, to imagine different types of suture thread with different characteristics of gauge, tensile strength, biocompatibility and biodegradability, according to whether they are intended for extensive lacerations (abdominal wall, thorax, lower limbs), or for small cuts and wounds as on the face, mouth and soft tissues. Some conditions require the material to be biocompatible but not biodegradable (as in cardiovascular surgery), while others necessitate both these characteristics (as in surgery to the urinary tract). The suture threads currently on the market vary first and foremost in the type of polymer with which they are made. Indeed, they vary from non-reabsorbable threads based on polyester, polypropylene, nylon and silk, such as Surgilene®, Surgilon®, Novafil® and Dermalon® by DG (Davis+Geck—American Cyanamid Company), to reabsorbable threads based on glycolic acid and collagen, such as Vicryl® and Catgut® by Ethicon (A. Pavan et al. "A Comparative Study of Poly(Glycolic acid) and Catgut as Suture Materials. Histomorphology and Mechanical Properties", Journal of Biomedical Materials Research, vol. 13, pages 477–496, 1979). As these materials all have a synthetic polymeric matrix, they are poorly biocompatible and only some of them are biodegradable, so they may cause inflammatory reactions at the lesion site where they are applied (E. A. Bakkum et al. "Quantitative analysis of the inflammatory reaction surrounding sutures commonly used in operative procedures and the relation to postsurgical adhesion formation" Biomaterials 1995, vol. 16, No. 17, pages 1283–1289) and may necessitate a second surgical operation to remove them from the application site. In particular the materials used to date to stitch wounds have given rise to an inflammatory response and hyperfibrotic process, because the organism recognises that they are foreign bodies. On account of this phenomenon, hypertrophic scars and keloids are prone to form around the stitches any of the anatomical or functional characteristics of healthy tissues. Apart from being unsightly, such scars may. If they are external, cause impairment of the motor functions. For examples if they occur on the joints such as the elbow or knee. When internal organs are stitched, the hyperfibrotic process may cause the formation of adhesions with the tissues surrounding the operation site.

Lastly, the use of ester derivatives of hyaluronic acid is known in the preparation of biomaterials, including suture threads, in the medical-surgical sector (European Patents EP 341745 and EP 216453).

"Eicosanyl": hyaluronic acid derivative with 75% of its carboxy functions esterified with benzyl alcohol, 20% esterified with eicosanyl alcohol (arachidyl alcohol; $CH_3(CH_2)_{18}$—$CH_2$—OH) and the remaining 5% salified with sodium. (obtained in example 4)

"Octadecyl": hyaluronic acid derivative with 75% of its carboxy functions esterified with benzyl alcohol and the remaining 25% esterified with octadecyl alcohol (stearyl alcohol; $CH_3$—$(CH_2)_{16}$—$CH_2$—OH) (obtained in example 3).

"Hexadecyl": hyaluronic acid derivative with 75% of its carboxy functions esterified with benzyl alcohol (and the remaining 25% esterified with hexadecyl alcohol (cetyl palmityl alcohol; $CH_3$—$(CH_2)_{14}$—$CH_2$—OH) (obtained in example 2).

"Dodecyl": hyaluronic acid derivative with 75% of its carboxy functions esterified with benzyl alcohol ($C_6H_5$—$CH_2OH$) and the remaining 25% esterified with dodecyl alcohol (Lauril alcohol; $CH_3$—$(CH_2)_{10}$—$CH_2$—OH) (obtained in example 1).

HYAFF 11: total ester of hyaluronic acid with benzylic alcohol (reference compound).

Figure 2:
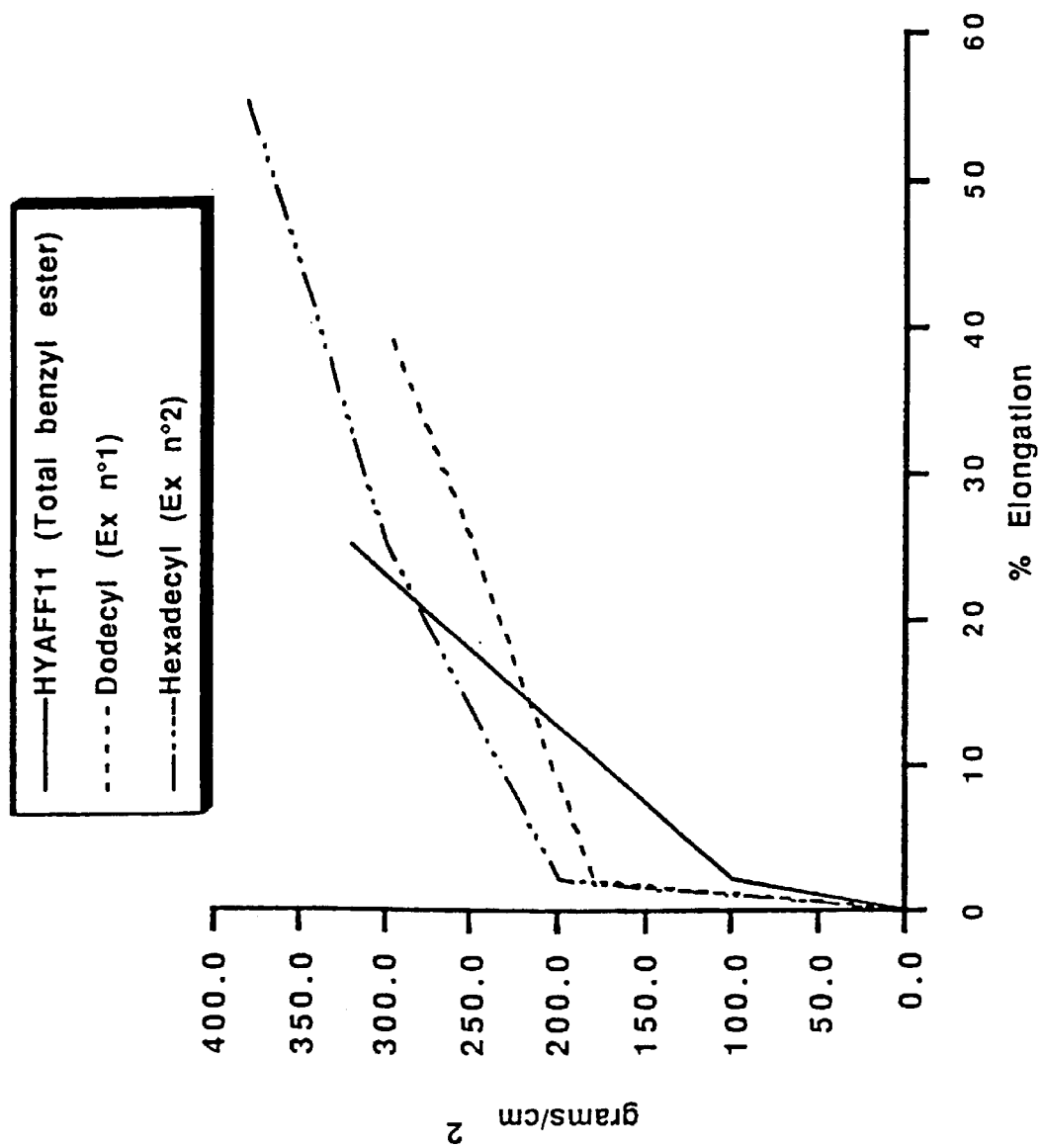

FIG. 2: testing the tensile properties of hyaluronic acid esters according to the present invention.

Figure 3:
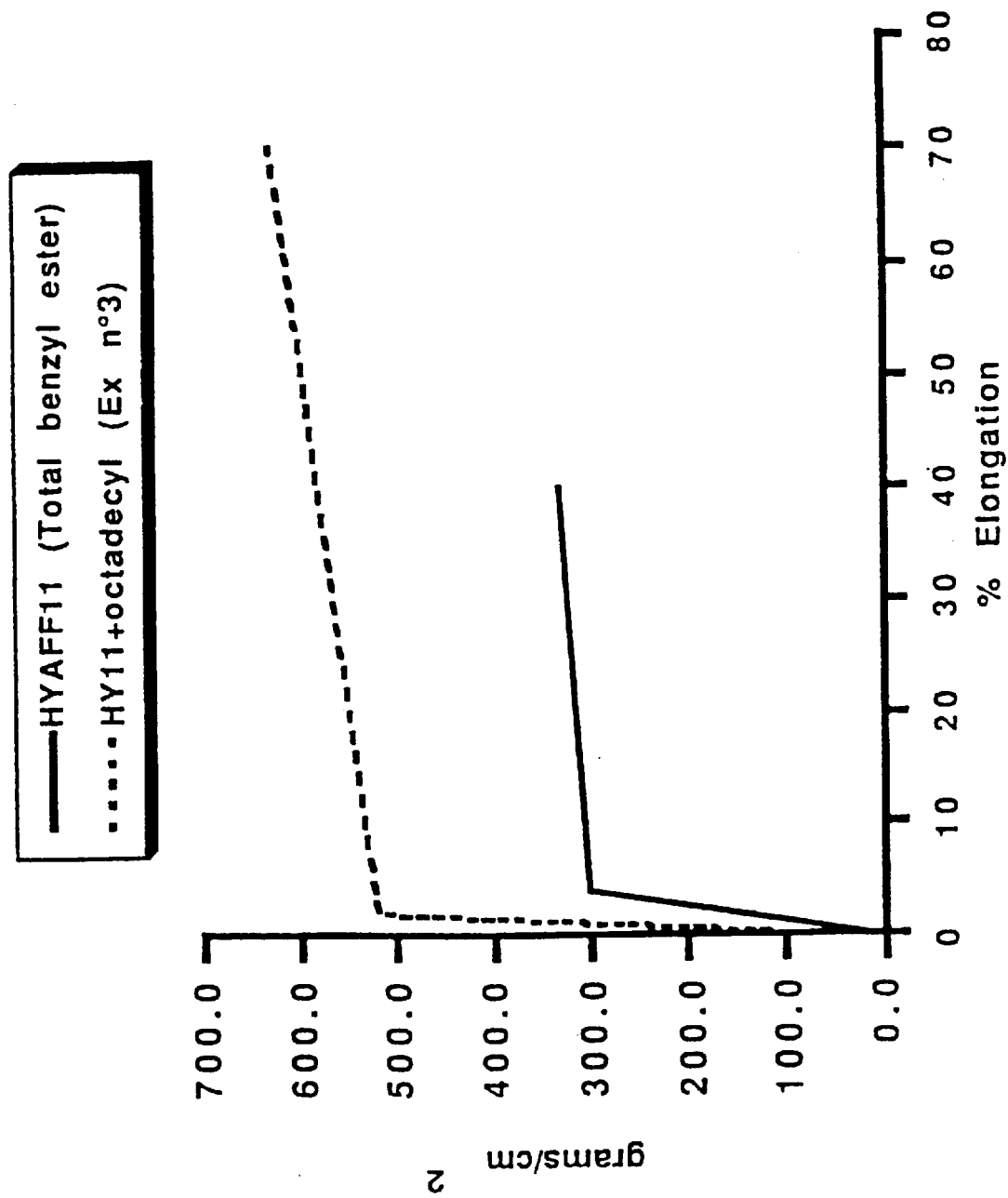

FIG. 3: Testing the dry tensile resistance of the multifilament made with the ester derivative prepared according to Example 3, compared with that of the multifilament based on the totally esterified benzyl ester (HYAFF 11).

Figure 4:
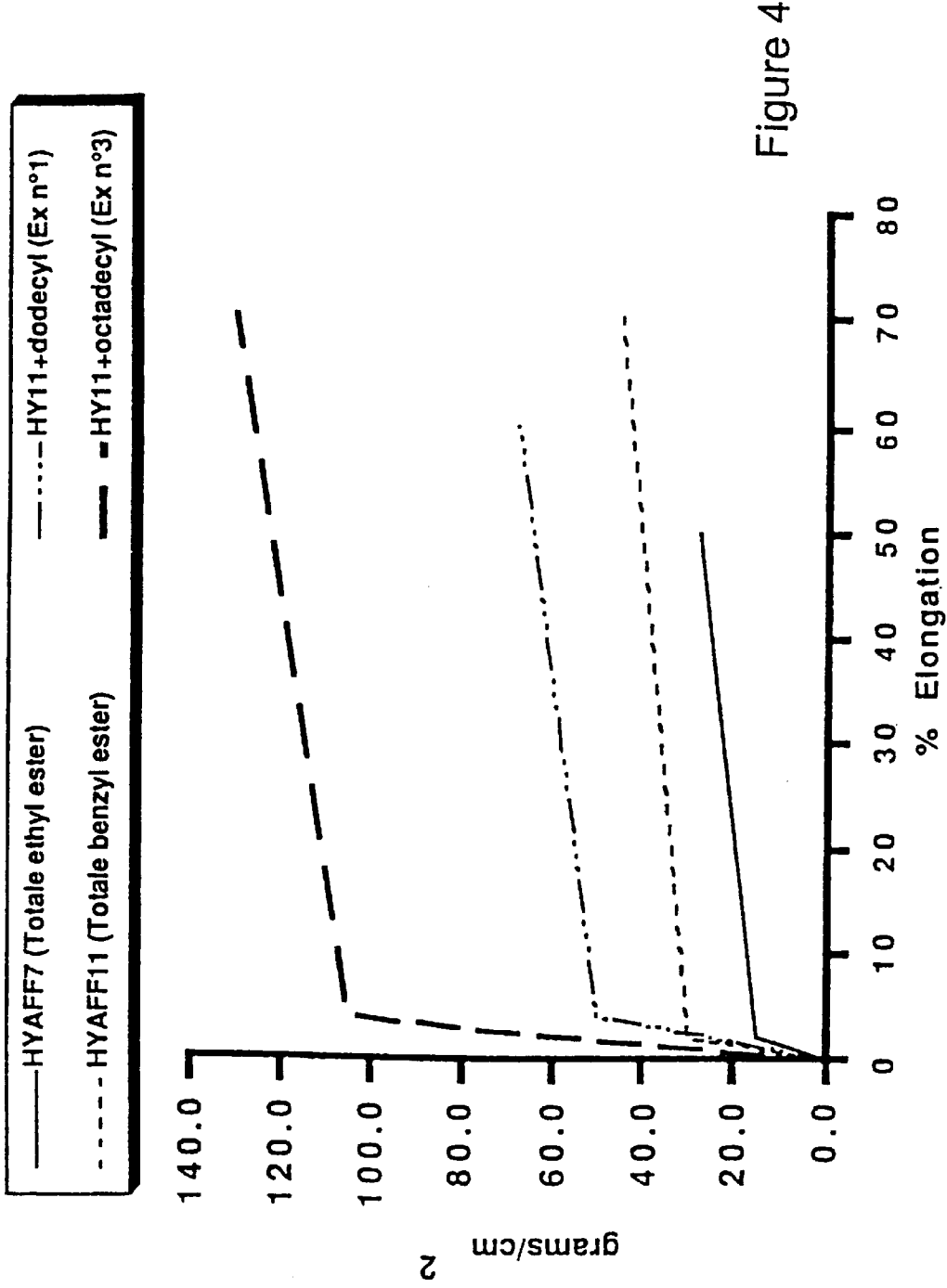

FIG. 4: Testing the wet tensile resistance of the threads made with the ester derivatives prepared according to Examples 1 and 3 compared with that of the threads based on totally esterified benzyl and ethyl esters (HYAFF 11 and Hyaff 7, respectively).

Figure 5:
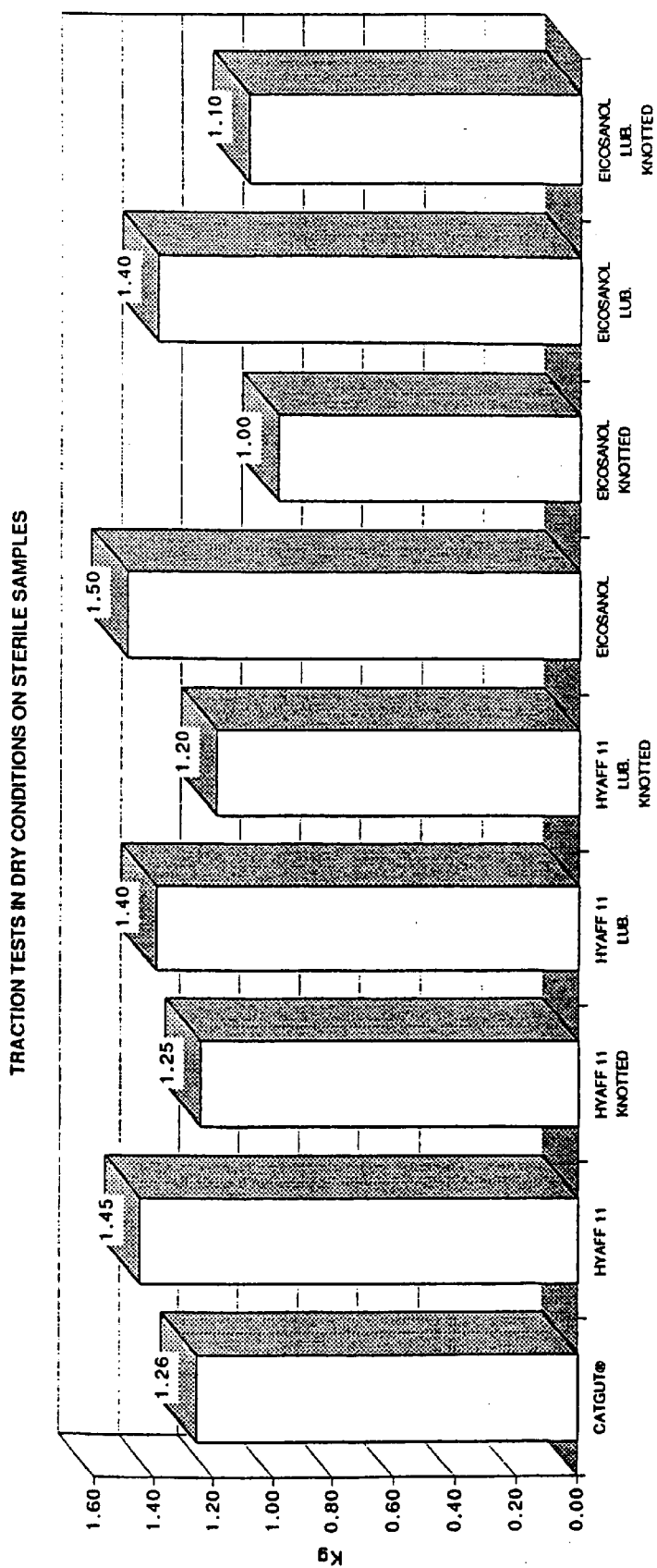

FIG. 5: comparing the tensile resistance of hyaluronic acid derivatives.

"HYAFF 11": multifilament thread made of the total benzylic ester of hyaluronic acid.

"EICOSANOL": multifilament thread made of the ester of hyaluronic acid obtained in example 4.

"CATGUT" chromic collagen monofilament for surgical suture.

Figure 6:
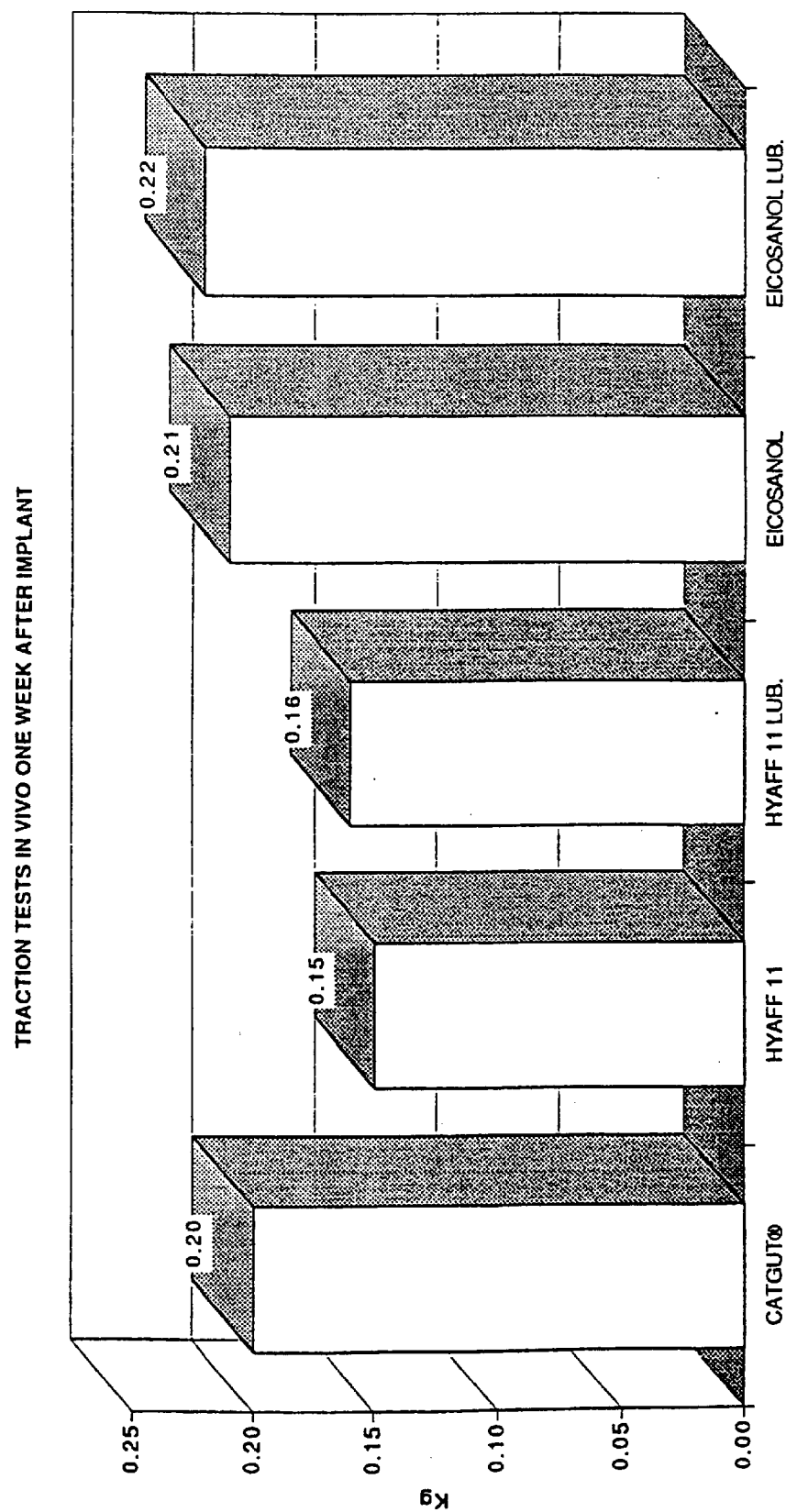

FIG. 6: resistance to tension one week after implant.

Figure 7:
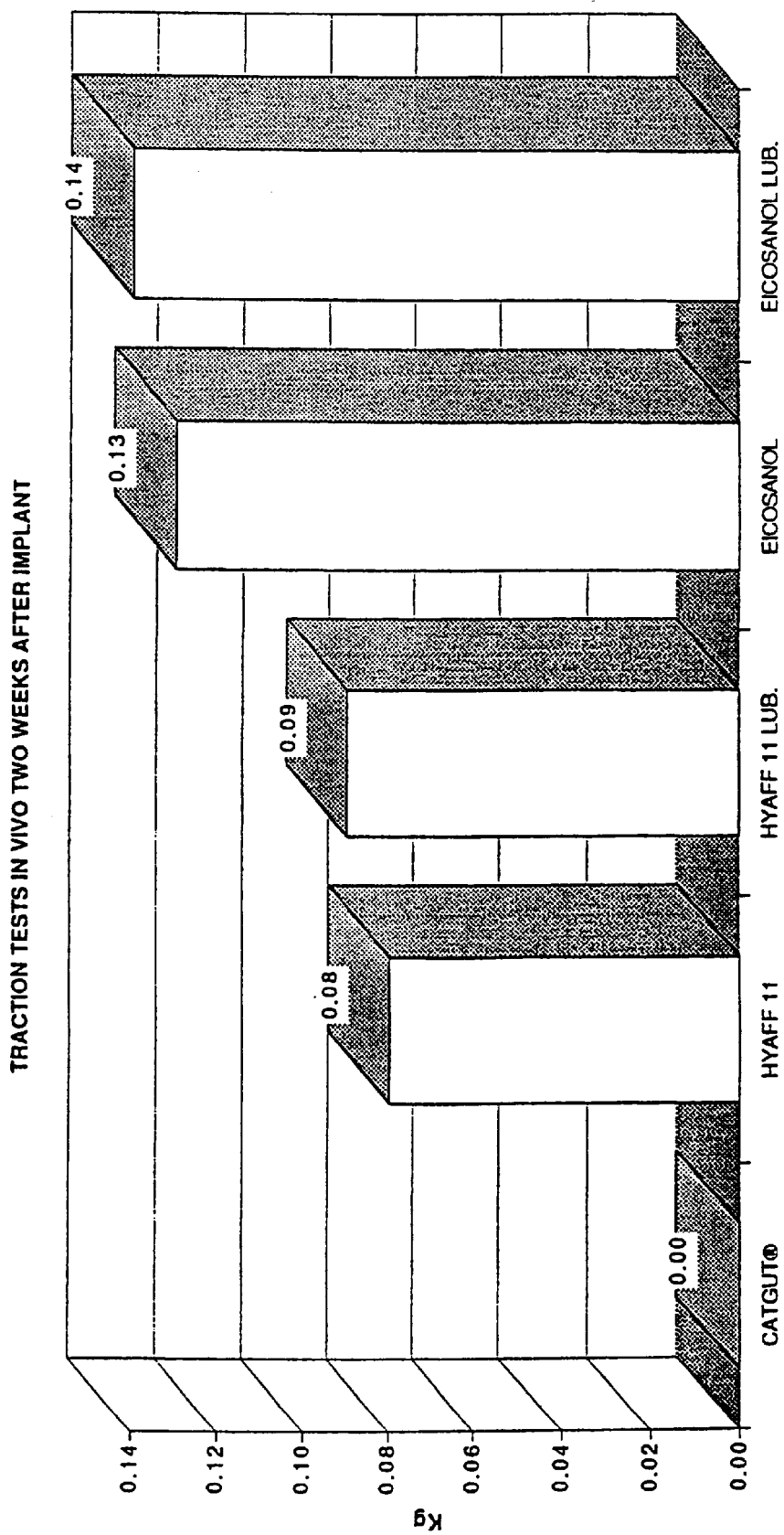

FIG. 7: resistance to tension two weeks after implant.

DISCLOSURE OF THE INVENTION

The present invention describes new ester derivatives of hyaluronic acid, wherein the first part of the carboxylic functions is esterified with an araliphatic alcohol, such as benzyl alcohol, and the second part with at least one long-chain, straight aliphatic alcohols with between 10 and 22 carbon atoms.

The hyaluronic acid which can be used in the present invention may be derived from any source, for example it may be obtained by extraction from rooster combs (EP 0138572; WO 92/18543), by fermentation (WO 95/04132) or by biotechnological means (WO 95/24497), and its molecular weight can range between 10,000 and 10,000,000 Da, particularly between 150,000 and 1,000,000 Da.

The long-chain aliphatic alcohols are those with a straight chain between 10 and 22 carbon atoms. The increase in the number of carbon atoms in the alkyl chain and the number of carboxylic functions involved in the esterification with the above said alcohols, yields ester derivatives of hyaluronic acid with an increasingly high degree of lipophilia generally leading to hydrophobic interactions when they come into contact with solutions or biological fluids, with the result that the tensile strength varies from one product to another as does the biodegradability time, according to the length of the lipid alcohol introduced.

Moreover the combination of the aliphatic and araliphatic esters on the hyaluronic acid molecule allows to obtain compounds showing good biodegradability and at the same time a significant medium-term tensile strength.

The extent of esterification with aliphatic alcohols may vary from 1 to 50%, and in particular between 10 and 25%. The extent of esterification with araliphatic alcohol may vary from 50 and 75%. A preferred araliphatic alcohol is benzyl alcohol.

The esterification with aliphatic and araliphatic alcohols may involve the totality or part of the available carboxylic functions of hyaluronic acid. In the latter case, the remaining non-esterified carboxylic functions are salified with alkaline, alkaline earth metals and quaternary ammonium salts. Sodium in particular is used.

The long alkyl chains introduced, with between 10 and 22 carbon atoms, give the ester derivatives of hyaluronic acid tensile properties never observed before and not foreseeable in other hyaluronic acid-based thread forms.

Indeed, besides having a biocompatible and biodegradable polysaccharide matrix, thus belonging to that class of compounds which, like hyaluronic acid, have bioplastic and pharmaceutical properties, they can be given varying degrees of lipophilia according to the use they are intended for. Their lipophilia can be adjusted by modulating the insertion of a lipid chain starting from the ester matrix itself (benzyl ester of hyaluronic acid, 50 to 75% esterified). Indeed, the increase in the lipid chain of the polymer (from $C_{10}$ to $C_{22}$) gives the material a structure with greater hydrophobic characteristics and modulates its degradation over time.

The present invention also relates to biocompatible threads in a multifilament conformation comprising filaments consisting of the hyaluronic mixed esters described above.

According to a preferred embodiment the biocompatible threads according to the present invention further comprise at least one filament of at least another biocompatible polymeric material. Among the preferred biocompatible synthetic polymeric materials we can mention polytetrafluoroethylene, polylactic acid and copolymers thereof, polyglycolic acid and copolymers thereof, polyhydroxyalkanoate such as polyhydroxybutyrrate obtained by fermentation of microorganisms, polycaprolactone, polyanhydrides, polyphosphazenes, polyaminoacids, polyurethanes, polycarbonates, polyorthoesters.

According to another preferred embodiment the biocompatible threads of the present invention are also biodegradable when they essentially consist of filaments constituted by the partial or total mixed esters of hyaluronic acid above described.

The present invention further relates to a process for the preparation of the biocompatible threads according to the present invention first involving the synthesis of partial or total mixed esters of hyaluronic acid. This can be done by esterification of a first part of the carboxylic functions of hyaluronic acid with an araliphatic alcohol, esterification of a second part of the carboxylic functions of hyaluronic acid with at least one $C_{10}$–$C_{22}$ straight alkyl chain alcohols, and salification of the possible remaining carboxylic functions not involved in the esterification steps.

The remaining steps to form the esters into threads are those commonly available in the field of thread preparation, e.g. via extrusion techniques. An application of these techniques is shown in the experimental part, example 6. When the biocompatible threads also comprise at least one filament of at least another biocompatible polymer, this process encompasses as the final step the association of the filaments consisting of the hyaluronic acid mixed esters according to the present invention with at least one filament of at least one synthetic biocompatible polymeric material.

The biocompatible threads according to the present invention can be used as suture threads. In fact suture threads containing filaments of the hyaluronic acid mixed esters according to the present invention in association with at least another biocompatible polymer such as those previously mentioned, do not cause the formation of hypertrophic scars or keloids. Preferred threads of this type are those having a tensile strength ranging from 200 to 4000 g/cm², more preferably from 250 to 2500 g/cm². The suture threads consisting essentially of filaments of the mixed esters of hyaluronic acid according to the present invention besides being biocompatible are also completely biodegradable and can inhibit the hypertrophic process that causes the formation of scarring. Given the excellent biodegradability of threads made of these esters, it is possible to avoid operating a second time to remove them.

These biodegradable threads show a diameter which varies between 75 and 800 micron and a tensile strength which varies, according to the ester derivative used, between 300 and 1800 g/cm².

Figure 1:
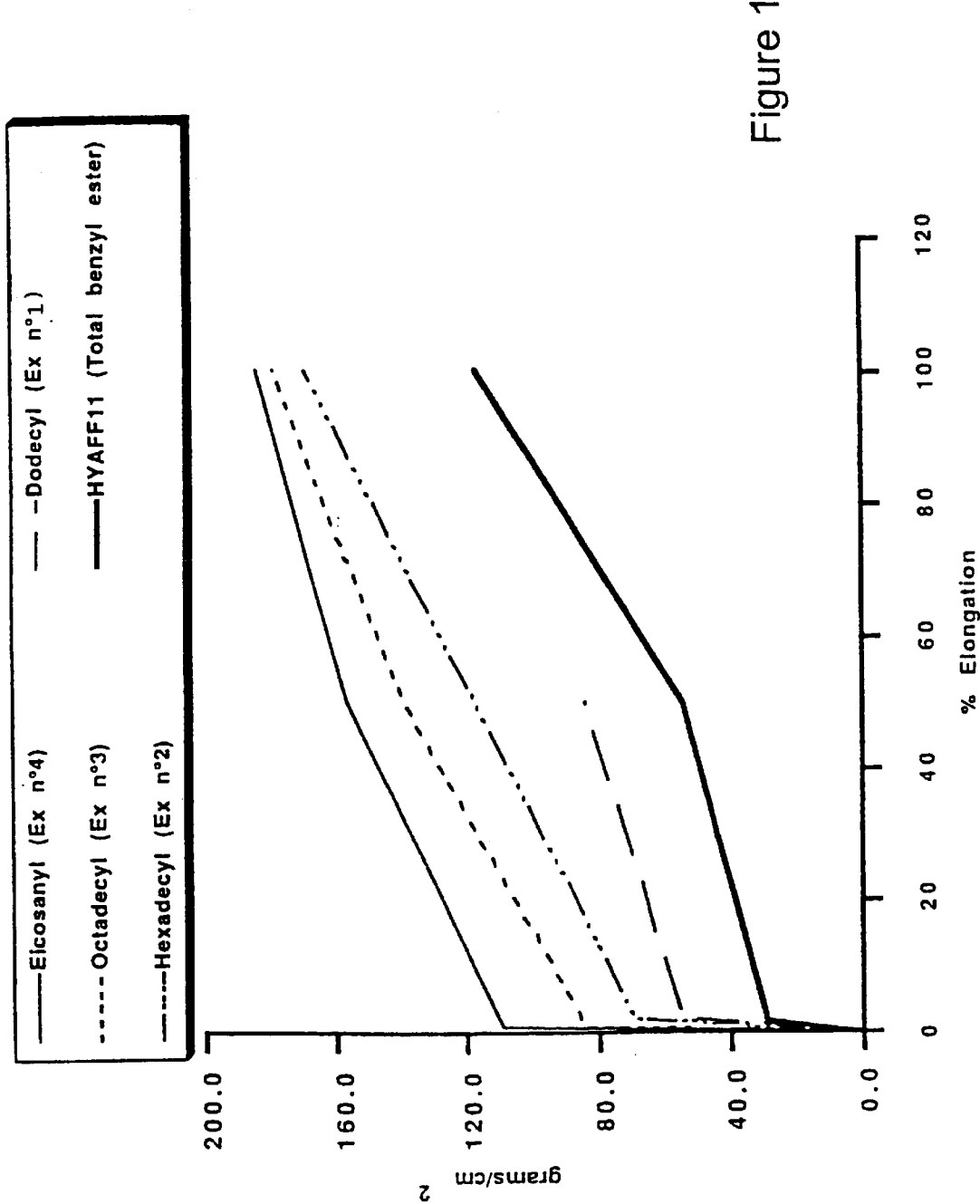
FIG. 1: Testing the tensile properties of hyaluronic acid esters according to the present invention.

The main characteristic of these materials is their strength which can be obtained on the basis of the following parameters:

the molecular weight of the starting hyaluronic acid;
the type of long-chain aliphatic alcohol used in the second esterification step;
the percentage of carboxylic groups involved in the esterification reaction with the long-chain lipid alcohol. FIG. 1 shows the different tensile properties of an ester derivative with benzyl alcohol of hyaluronic acid (HYAFF 11) from those of the derivatives of the present invention (examples 1–4) in a wet environment (saline solution), particularly as the substituted alkyl chain increases (dodecyl alcohol; hexadecyl alcohol; octadecyl alcohol; eicosanyl alcohol).

The threads thus constituted can be used to advantage in surgery, such as in maxillofacial surgery, in suture to tissues requiring a long degradation time, as in the case of materials which come into constant contact with biological fluids, or tissues requiring rapid degradation, as in the case of contact with soft tissues such as occurs in plastic surgery, as fillers in aesthetic surgery, and in dentistry.

Moreover, due to their content in hyaluronic acid derivatives, the threads according to the invention are able to act as bacteriostats and to limit the proliferation of inflammatory cells.

Lastly the threads according to the present invention can be processed to form gauze, meshes, non woven fabrics, tubes and association of the same for use in surgery in the preparation of biomaterials, health care products and as scaffold for cells cultures.

Experimental Part

The tensile properties of the ester derivatives of hyaluronic acid have been assessed using a computerized tensiometer T-10 from MONSANTO, an instrument which can control the tensile stress applied to a given material. Generally speaking, the tensile properties of a material are measured according to its resistance to stress. When calculating tensile resistance, three main correlated values must be considered:

load at break, elongation at break and shear modulus.
load at break gives the amount of stress necessary to cause the thread to break.
elongation at break is the extent to which the thread is stretched when it breaks.
the shear modulus represents the amount of stress which must be applied before the thread begins to stretch.

The shear modulus is, therefore, correlated with the elongation of the thread. Indeed, the greater the elastic properties of the thread, the higher the percentage of elongation at breaking point.

In particular, according to the variations in the lipid chain which was introduced, the ester derivatives of hyaluronic acid reported hereafter showed more marked elongation as the number of carbon atoms in the alcohol increased. Indeed, processing of the data reported in FIG. 2 showed that the various hyaluronic acid ester threads presented various degrees of elongation. In the case of the benzyl ester derivative, elongation was virtually nil, while the dodecyl and hexadecyl derivatives showed an increase in elongation of the material which was proportional to the lipid chain introduced (hexadecyl>dodecyl).

EXAMPLE 1

Preparation of a hyaluronic acid derivative with 75% of its carboxy functions esterified with benzyl alcohol ($C_6H_5$—$CH_2OH$) and the remaining 25% esterified with dodecyl alcohol (lauryl alcohol; $CH_3$—$(CH_2)_{10}$—$CH_2$—$OH$).

6.21 gr of tetrabutyl ammonium salt of hyaluronic acid with a molecular weight of 180,000 Da (10 meq) is solubilized in 248 ml of dimethylsulfoxide (DMSO) at room temperature. This solution is supplemented with 0.89 ml of benzyl bromide (7.5 meq) and then warmed to 30° C. for 12 hours. It is then allowed to return to room temperature and supplemented with 0.62 gr. of dodecyl bromide (2.5 meq). It is rewarmed to 30° C. for 24 hours. A solution of 2.5% (w/w) of NaCl in water is then added and the resulting mixture is poured into 750 ml of acetone under agitation. A precipitate is formed which is filtered and washed three times in 100 ml of acetone/water 5:1, three times with 100 ml of acetone and then vacuum-dried for 24 hours at 30° C. 4.8 gr. of the desired product is thus obtained. Quantitative determination of the benzyl alcohol and dodecyl alcohol content is performed by gas chromatography after alkaline hydrolysis. The total ester group content is quantified by the saponification method described on pages 169–172 of "Quantitative organic analysis via functional groups" 4th edition (J. Wiley & Sons Publication).

EXAMPLE 2

Preparation of a hyaluronic acid derivative with 75% of its carboxylic functions esterified with benzyl alcohol (and the remaining 25% esterified with hexadecyl alcohol (cetyl palmityl alcohol; $CH_3$—$(CH_2)_{14}$—$CH_2$—$OH$).

6.21 gr. of tetrabutyl ammonium salt of hyaluronic acid with a molecular weight of 180,000 Da (10 meq) is solubilized in 248 ml of dimethylsulfoxide (DMSO) at room temperature. This solution is supplemented with 0.89 ml of benzyl bromide (7.5 meq) and then warmed to 30° C. for 12 hours. It is then allowed to return to room temperature and supplemented with 0.76 gr. of hexadecyl bromide (2.5 meq). It is rewarmed to 30° C. for 24 hours. A solution of 2.5% (w/w) of NaCl in water is then added and the resulting mixture is poured into 750 ml of acetone under agitation. A precipitate is formed which is filtered and washed three times in 100 ml of acetone/water 5:1, three times with 100 ml of acetone and then vacuum-dried for 24 hours at 30° C. 5 gr. of the desired product is thus obtained. Quantitative determination of the benzyl alcohol and hexadecyl alcohol content is performed by gas chromatography after alkaline hydrolysis. The total ester group content is quantified by the saponification method described on pages 169–172 of "Quantitative organic analysis via functional groups" 4th edition (J. Wiley & Sons Publication).

EXAMPLE 3

Preparation of a hyaluronic acid derivative with 75% of its carboxy functions esterified with benzyl alcohol and the remaining 25% esterified with octadecyl alcohol (stearyl alcohol; $CH_3$—$(CH_2)_{16}$—$CH_2$—$OH$).

6.21 gr of tetrabutyl ammonium salt of hyaluronic acid with a molecular weight of 180,000 Da (10 meq) is solubilized in 248 ml of dimethylsulfoxide (DMSO) at room temperature. This solution is supplemented with 0.89 ml of benzyl bromide (7.5 meq) and then warmed to 30° C. for 12 hours. It is then allowed to return to room temperature and supplemented with 0.83 gr. of octadecyl bromide (2.5 meq). It is rewarmed to 30° C. for 24 hours. A solution of 2.5% (w/w) of NaCl in water is then added and the resulting mixture is poured into 750 ml of acetone under agitation. A precipitate is formed which is filtered and washed three times in 100 ml of acetone/water 5:1, three times with 100 ml of acetone and then vacuum-dried for 24 hours at 30° C. 5.1 gr. of the desired product is thus obtained. Quantitative determination of the benzyl alcohol and octadecyl alcohol content is performed by gas chromatography after alkaline hydrolysis. The total ester group content is quantified by the saponification method described on pages 169–172 of "Quantitative organic analysis via functional groups" 4th edition (J. Wiley & Sons Publication).

EXAMPLE 4

Preparation of a hyaluronic acid derivative with 75% of its carboxy functions esterified with benzyl alcohol, 20% esterified with eicosanyl alcohol (arachidyl alcohol; $CH_3$ $(CH_2)_{18}$—$CH_2$—$OH$) and the remaining 5% salified with sodium.

6.21 gr. of tetrabutyl ammonium salt of hyaluronic acid with a molecular weight of 180,000 Da (10 meq) is solubilized in 248 ml of dimethylsulfoxide (DMSO) at room temperature. This solution is supplemented with 0.89 ml of benzyl bromide (7.5 meq) and then warmed to 30° C. for 12 hours. It is then allowed to return to room temperature and supplemented with 0.72 gr. of eicosanyl bromide (2 meq). It is rewarmed to 30° C. for 24 hours. A solution of 2.5% (w/w) of NaCl in water is then added and the resulting mixture is poured into 750 ml of acetone under agitation. A precipitate is formed which is filtered and washed three times in 100 ml of acetone/water 5:1, three times with 100 ml of acetone and then vacuum dried for 24 hours at 30° C. 5 gr. of the desired product is thus obtained. Quantitative determination of the benzyl alcohol and eicosanyl alcohol content is performed by gas chromatography after alkaline hydrolysis. The total ester group content is quantified by the saponification method described on pages 169–172 of "Quantitative organic analysis via functional groups" 4th edition (J. Wiley & Sons Publication).

EXAMPLE 5

Preparation of a hyaluronic acid derivative with 75% of its carboxy functions esterified with benzyl alcohol, 15% esterified with docosanyl alcohol ($CH_3$—$(CH_2)_{20}$—$CH_2$—OH) and the remaining 10% salified with sodium.

6.21 gr of tetrabutyl ammonium salt of hyaluronic acid with a molecular weight of 180,000 Da (10 meq) are solubilized in 248 ml of dimethylsulfoxide (DMSO) at room temperature. This solution is supplemented with 0.89 ml of benzyl bromide (7.5 meq) and then warmed to 30° C. for 12 hours. It is then allowed to return to room temperature and supplemented with 0.58 gr. of docosanyl bromide (1.5 meq). It is rewarmed to 30° C. for 24 hours. A solution of 2.5% (w/w) of NaCl in water is then added and the resulting mixture is poured into 750 ml of acetone under agitation. A precipitate is formed which is filtered and washed three times in 100 ml of acetone/water 5:1, three times with 100 ml of acetone and then vacuum-dried for 24 hours at 30° C. 4.9 gr. of the desired product is thus obtained. Quantitative determination of the benzyl alcohol and docosanyl alcohol content is performed by gas chromatography after alkaline hydrolysis. The total ester group content is quantified by the saponification method described on pages 169–172 of "Quantitative organic analysis via functional groups" 4th edition (J. Wiley & Sons Publication).

EXAMPLE 6

Preparation of a multifilament from the hyaluronic acid derivative prepared according to Example 3.

The ester derivative prepared according to Example 3 is solubilized in DMSO to a concentration of 150 mg/ml at a temperature of 30° C. The solubilized derivative is filtered through a 20 micron mesh and placed in an extrusion reactor connected to a spinneret with 100 80-micron holes. The product is extruded in a coagulation bath containing a solvent which allows the DMSO to be extracted from the product (for example, ethanol), and the material coming out of the spinneret is wound onto a series of drafting bobbins and blown dry.

EXAMPLE 7

Testing the dry tensile resistance of the multifilament made with the ester derivative prepared according to Example 3, compared with that of the multifilament based on the totally esterified benzyl ester (HYAFF 11).

The ester derivative prepared according to example 3 is processed according to the procedure described in Example 6 and the multifilament thus obtained is placed under stress to measure its tensile resistance. A T10 Tensiometer from Monsanto is used for this purpose. The results obtained are shown in FIG. 3. As can be seen, the "lipid" derivative presented better resistance to stress than the multifilament based on the totally esterified benzyl ester did.

EXAMPLE 8

Testing the wet tensile resistance of the threads made with the ester derivatives prepared according to Examples 1 and 3 compared with that of the threads based on totally esterified benzyl and ethyl esters (HYAFF 11 and HYAFF 7, respectively).

The ester derivatives prepared according to Examples 1 and 3 are processed according to the procedure described in Example 6. The threads thus obtained are immersed for 15 hours in an aqueous solution of 0.9% NaCl w/v and then placed under stress to measure their tensile resistance. A T10 Tensiometer from Monsanto is used for this purpose. The results obtained are shown in FIG. 4. As can be seen, the "lipid" derivative presented different resistance to stress, as the chain introduced was varied (dodecyl<octadecyl), from that shown by the threads obtained with the HYAFF 11 and HYAFF 7 derivatives.

EXAMPLE 9

Testing the tensile resistance of the threads constituted by a hyaluronic acid derivative with 75% of its carboxylic functions esterified with benzyl alcohol, 20% esterified with eicosanyl alcohol (arachidyl alcohol $CH_3$_$(CH_2)_{18}$—$CH_2OH$) and the remaining 5% salified with sodium following in vivo implantation in an animal model Materials
    multifilament thread of total benzyl ester of hyaluronic acid (HYAFF 11);
    multifilament thread of the hyaluronic acid derivative according to Example 4 (HYAFF11/p75+eicosanyl alcohol);
    chromic monofilament for surgical suture, CATGUT® (collagen);
    biocompatible and biodegradable lubricant SQUALANO, Aldrich;
    T-10 Tensiometer by Monsanto.

Description

Subcutaneous implant was performed on 14 S. D. Harlan rats using the following types of suture on each rat: HYAFF 11, HYAFF 11 lubricated with Squalane, HYAFF 11/p75+eicosanyl alcohol, HYAFF 11/p75+eicosanyl alcohol lubricated with Squalane and CATGUT® commercial sutures.

The threads were lubricated with a lipophilic substance such as Squalane, a saturated aliphatic hydrocarbide of natural origin with 30 carbon atoms, to assess whether this type of treatment affords better protection from biological liquids.

The rats were subdivided into two groups and sacrificed after 7 and 14 days respectively to assess the tensile characteristics of the threads.

FIG. 5 compares the tensile resistance of derivatives HYAFF 11 and HYAFF11/p75+eicosanyl alcohol, both lubricated and not lubricated, with that of CATGUT® commercial suture before implant.

The tensile characteristics of the materials are similar.

FIG. 6 shows the decreased resistance to tension one week after implant. The commercial suture and that of HYAFF11/p75+eicosanyl alcohol presented similar behaviour and the lubricated threads were the most resistant.

FIG. 7 shows the results two weeks after implant. As can be seen, it was impossible to remove the CATGUT® suture from the site in order to test it for tensile resistance because it was completely degraded. The threads of HYAFF11/p75+eicosanyl alcohol, on the other hand, presented tensile resistance which was 60% greater than that of the HYAFF 11 threads.

EXAMPLE 10

Preparation of a mixed multifilament by extrusion of the hyaluronic acid derivative prepared according to example 4 and its combination with a polycaprolactone monofilament.

The ester derivative prepared according to Example 4 is solubilized at a concentration of 150 mg/ml in DMSO at a temperature of 30° C. The solubilized derivative is filtered through a 20 micron-mesh and placed in an extrusion reactor connected to a spinneret with 100 80 microns-holes. The material extruded by the spinneret passes into a coagulation bath containing a solvent which serves to extract DMSO (e.g. ethanol) and at the same time it is associated with a monofilament of polycaprolactone with a thickness of 20 microns. The combined strands are wound onto a series of drafter rollers connected with blow driers to dry the threads.

EXAMPLE 11

Preparation of a mixed multifilament by extrusion of the hyaluronic acid derivative prepared according to example 3 and its combination with a multifilament of PTFE.

The ester derivative prepared according to example 3 is solubilized to a concentration of 150 mg/ml in DMSO at a temperature of 30° C. The solubilized derivative is filtered through a 20 micron-mesh and placed in an extrusion connected to a spinneret with a 100 80 micron-holes. The material extruded by the spinneret passes into a coagulation bath containing a solvent which serves to extract the DMSO (e.g. ethanol) and at the same time it is associated with a multifilament of PTFE obtained by hot extrusion, with the aid of a spinneret with 100 10 microns-holes. The combined strands are wound onto a series of drafter rollers connected with blow driers to dry the threads.

EXAMPLE 12

Preparation of a mixed multifilament by extrusion of the hyaluronic acid derivative prepared according to example 5, with a polylactide multifilament.

The ester derivative according to example 5 is solubilized to a concentration of 150 mg/ml in DMSO at a temperature of 30° C. The solubilized derivative is filtered through a 20-micron mesh and placed in an extrusion reactor connected to a spinneret with 100 80 microns-holes. The material extruded by the spinneret passes into a coagulation bath containing a solvent which serves to extract the DMSO (e.g. ethanol) and at the same time it is associated with a polylactide multifilament obtained by dry extrusion from a concentrated solution of the polymer in a suitable solvent (e.g. methylene chloride). With the strands making up the multifilament having a mean diameter of 10 microns. The combined strands are wound onto a series of drafter rollers connected to blow dryers to dry the threads.

EXAMPLE 13

Preparation of a braided thread from the combination of multifilaments obtained from the ester derivative prepared according to example 2 and a strand of polycaprolactone, with the strands making up the multifilament having a mean diameter of 15 microns.

Using a textile braiding machine, three multifilaments of the ester derivative prepared according to example 2 are braided together with a multifilament of polycaprolactone obtaining a mixed thread, with the strands making up the multifilament having a final mean diameter of 12,5 microns.

What is claimed is:

1. Biocompatible threads having a multifilament conformation comprising filaments consisting of ester derivatives of hyaluronic acid, wherein a first part of the carboxylic function is esterified with an araliphatic alcohol, a second part is esterified with at least one long-chain, straight aliphatic alcohol with between 10 and 22 carbon atoms, and wherein any non-esterified carboxylic function is salified.

2. The biocompatible threads according to claim 1 further comprising filaments consisting of at least another biocompatible polymeric material selected from the group consisting of polyhydroxyalkalonate, PTFE, polyglycolic acid and a copolymer thereof, polylactic acid and a copolymer thereof, polycaprolactone, polyorthoesters, polyanhydrides, polyphosphazene, polyaminoacid, polyurethane, polycarbonate having tensile strength of 200–4000 g/cm$^2$.

3. The biodegradable threads according to claim 2, having a tensile strength ranging from 250 to 2500 g/cm$^2$.

4. The biocompatible threads according to claim 1 whose filaments consist essentially of said hyaluronic ester derivatives and having a tensile strength which varies, according to the ester derivative used, between 300 and 1800 g/cm$^2$.

5. The biocompatible threads according to claim 1, wherein said araliphatic alcohol is benzyl alcohol.

6. The biocompatible threads according to claim 1, wherein said long-chain straight aliphatic alcohol is chosen from the group consisting of decyl, dodecyl, hexadecyl, octadecyl, eicosyl, docosyl, alcohol.

7. The biocompatible threads according to claim 1, wherein the percentage of the carboxylic functions of hyaluronic acid esterified with araliphatic alcohols varies between 50 and 75%.

8. The biocompatible threads according to claim 1, wherein the percentage of carboxylic functions esterified with long-chain aliphatic alcohols is comprised between 10 and 25%.

9. The biocompatible threads according to claim 1, wherein the remaining carboxy functions are salified with alkaline, alkaline earth metals, and quaternary ammonium salts.

10. The biocompatible threads according to claim 9, wherein the remaining carboxylic functions are salified with sodium.

11. The biocompatible threads according to of claim 1, wherein the hyaluronic acid has a molecular weight of between 10,000 and 10,000,000 Da.

12. The biocompatible threads according to claim 1, wherein hyaluronic acid has a molecular weight of between 150,000 and 1,000,000 Da.

13. The biocompatible threads according to claim 4, having a diameter which varies between 75 and 800 microns.

14. Biomaterials, health-care products, surgical articles and scaffold for cell cultures in the form of gauzes, meshes, non-woven fabrics, tubes and association thereof containing the biocompatible threads according to claim 1.

15. A process for preparing the biocompatible threads according to claim 4, comprising the following steps:
    a) esterifying a first part of the carboxylic functions of hyaluronic acid with an araliphatic alcohol,
    b) esterifying the remaining carboxylic functions with at least one aliphatic long chain straight alcohol with between 10 and 4 carbon atoms;
    c) salifying the possible remaining carboxylic functions of hyaluronic acid not involved in the preceding esterification steps,
    d) subjecting the hyaluronic mixed esters obtained in step c) to conventional thread-forming processes.

16. A process for preparing the biocompatible threads according to claim 2, comprising the following steps:
    a) esterifying a first part of the carboxylic functions of hyaluronic acid with an araliphatic alcohol, b) esterifying the remaining carboxylic functions with at least one aliphatic long chain straight alcohol with between 10 and 22 carbon atoms;

c) salifying the possible remaining carboxylic functions of hyaluronic acid not involved in the preceding esterification steps, d) subjecting the hyaluronic mixed esters obtained in step c) to conventional thread-forming processes;

e) associating the threads having a multifilament conformation whose filaments consist essentially of said hyaluronic ester derivatives and coming from step d), with at least one filament consisting of at least one biocompatible synthetic polymeric material selected from the group consisting of: polyhydroxyalkalonate, PTFE, polyglycolic acid and copolymers thereof, polylactic acid and a copolymer thereof, polycaprolactone, polyorthoesters, polyanhydrides, polyaminoacids, polyphosphazene, polyurethane, polycarbonate having tensile strength of 200–4000 g/cm$^2$.

17. A suture method comprising stitching wounds following to general surgery operations, maxillofacial surgery operations, plastic surgery operation, aesthetic surgery operations, and dentistry operations, with the biocompatible threads according to claim 1.

18. Fillers for esthetic surgery comprising the biocompatible threads according to claim 1.

* * * * *